United States Patent
De Wan et al.

[11] Patent Number: 5,847,107
[45] Date of Patent: Dec. 8, 1998

[54] METHOD OF PREPARING MIXED GLUCOSAMINE SALTS

[75] Inventors: Maura De Wan, Morbio Inferiore; Giuseppe Volpi, Massagno, both of Switzerland

[73] Assignee: Rotta Research B.V. Amsterdam (Swiss Branch), Lugano, Switzerland

[21] Appl. No.: 910,749

[22] Filed: Aug. 13, 1997

[30] Foreign Application Priority Data

Aug. 19, 1996 [CH] Switzerland ............... 2024/96

[51] Int. Cl.⁶ ............... C07H 5/06; C07H 1/00
[52] U.S. Cl. ............... 536/55.3; 514/62; 536/55.2
[58] Field of Search ............... 514/62; 536/17.2, 536/17.9, 29.1, 55.2, 55.3

[56] References Cited

U.S. PATENT DOCUMENTS 4,642,340   2/1987   Senin et al. ............... 536/55.2

FOREIGN PATENT DOCUMENTS 893010      8/1982   Belgium .
444000      8/1991   European Pat. Off. .
3532081 A1  3/1987   Germany .
89-05646    6/1989   WIPO .

Primary Examiner—Marian C. Knode
Assistant Examiner—Howard C. Lee
Attorney, Agent, or Firm—Sughrue, Mion, Zinn, Macpeak & Seas, PLLC

[57] ABSTRACT

A method of preparing a therapeutically active crystalline form of glucosamine sulphate which is stable at ambient temperature and humidity and corresponds to the empirical formula:

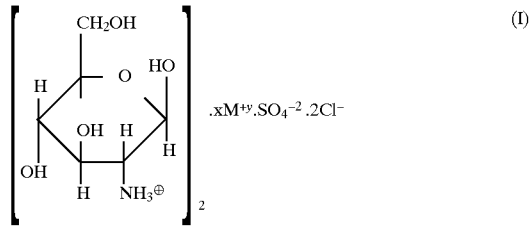

in which M represents a metal selected from the group consisting of Na, K, Ca, Mg, x=1 if y=2, and x=2 if y=1, wherein glucosamine hydrochloride and a sulphate of a metal selected from Na, K, Ca, Mg are reacted in the stoichiometric ratio defined by formula (I), in an aqueous solvent, and the stable crystalline form is precipitated by the addition of a liquid precipitating agent miscible with water.

5 Claims, No Drawings

METHOD OF PREPARING MIXED GLUCOSAMINE SALTS

BACKGROUND OF THE INVENTION

1. Field of the Invention

The present invention relates to a novel and advantageous method of synthesizing mixed glucosamine salts, including in their formula, protonated glucosamine and an alkali-metal or alkaline-earth ion such as sodium, potassium, calcium or magnesium as cations and chlorides and sulphates as negative ions.

The minimum empirical formula of the above mentioned salts may be represented as follows:

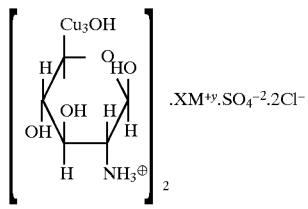

wherein

M represents Na, K, Ca, or Mg and x=1 if y=2 x=2 if y=1

These mixed salts are in crystalline form with melting points above 300° C. and are stable at ambient temperature and humidity.

2. Background Information

Glucosamine sulphate is a well known substance which is extremely important in the treatment of both acute and chronic rheumatic and arthritic diseases and arthrosis and, in fact, in all pathological conditions originating from metabolic dysfunctions affecting bone and joint tissue.

The synthesis of glucosamine sulphate was described by Breuer in 1898 (Chem. Ber. 31, 2197) and an industrial method forms the subject of GB 1,056,331, of U.S. Pat. No. 3,683,076, and of Swiss patent 525, 861.

However, this substance has some disadvantages, such as the fact that it is highly hygroscopic, and the ease with which the amine group is oxidized when it is not completely salified, which render it practically impossible to use in the preparation of pharmaceutical forms for use in human therapy.

Oral forms such as tablets, capsules and powders therefore require the presence of antioxidants in their formulations, but these do not solve the problem of hygroscopicity; it is then necessary to prepare these forms in environments with a relative humidity no greater than 30%, with still unsatisfactory results, the instability of these forms over time rendering them practically impossible to use.

Similar remarks apply to rectal forms (suppositories) which degrade very quickly, even if kept in dry and refrigerated environments.

Injectable forms are sufficiently stable for practical purposes, however difficulties apply to their preparation. It is not possible to prepare lyophilized forms because, invariably, one obtains products which have the appearance and consistency of viscous oils and, as such, are practically unusable.

The problems of glucosamine sulphate, which are such as to preclude its practical use for treatment in man, were overcome by the invention of glucosamine-SP and of the method of preparation thereof described in U.S. Pat. No. 4,642,340.

Glucosamine-SP is a mixed salt in the formula of which protonated glucosamine and the Na$^+$ ion appear as cations and the chloride and the sulphate ions as anions, according to the following empirical formula:

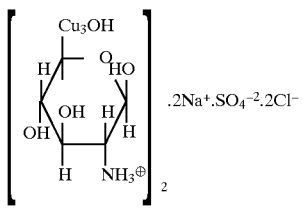

This is a non-hygroscopic, crystalline substance with a melting point above 300° C., which is stable in normal conditions of temperature and relative humidity. It also has pharmacological properties practically identical to those of glucosamine sulphate with the advantage of being easily usable in the preparation of oral and parenteral pharmaceutical forms for use in human therapy.

The method of preparation of glucosamine-SP described in U.S. Pat. No. 4,642,340 consists essentially of dissolving glucosamine sulphate and sodium chloride in distilled water and separating the glucosamine-SP by the addition of water-soluble liquid precipitating agents in which glucosamine sulphate has a solubility no greater than 0.1% (w/v). Acetone, ethanol, acetonitrile, tetrahydrofuran and dioxane are mentioned as precipitating agents in the examples. Moreover, in the patent, the volumetric ratios between the solvent and precipitating agents, as well as the other reaction parameters such as temperatures, contact times and stirring speeds, are strictly fixed.

The glucosamine sulphate which is used as the starting product in the synthesis of glucosamine-SP is in turn produced from glucosamine hydrochloride, according to Swiss patent 525, 861, by a synthesis which consists essentially of two steps which can be summarised as follows:

1. Liberation of the alpha form of glucosamine from its salt with hydrochloric acid in an aqueous-alcoholic medium, in the presence of triethylamine.

2. Salification of the alpha form of glucosamine with the stoichiometric quantity of sulphuric acid in an ethyl ether medium to produce glucosamine sulphate.

The entire process which leads to the synthesis of glucosamine-SP, described in the patent U.S. Pat. No. 4,642,340 from glucosamine hydrochloride can therefore be represented schematically by the following 3 steps:

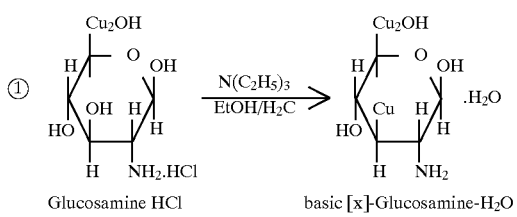

-continued

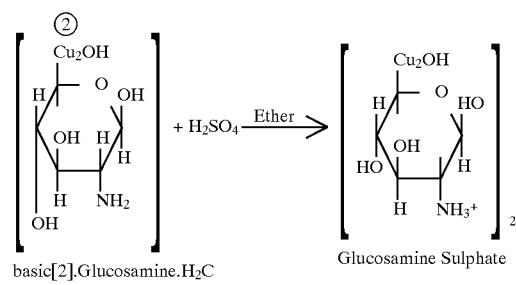

basic[2].Glucosamine.H2C

Glucosamine Sulphate

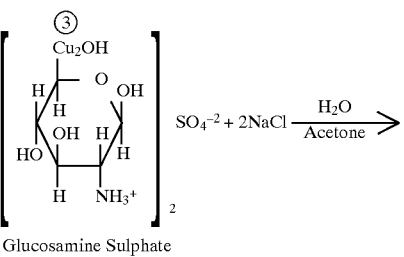

Glucosamine Sulphate

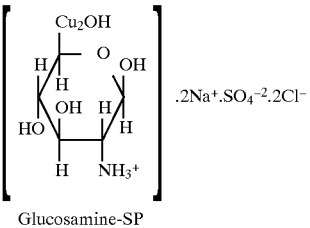

Glucosamine-SP

SUMMARY OF THE INVENTION

The present patent application describes a novel method of synthesising mixed glucosamine salts, amongst which glucosamine-SP is also included. It has the advantage of producing this substance and its analogues, in the molecular formula of which not only sodium but other alkali-metal and alkaline-earth elements such as K, Ca and Mg may appear alternatively as cations, in a single step from glucosamine hydrochloride.

This method avoids the steps of liberating the basic glucosamine from its hydrochloride and subsequent salification with sulphuric acid, rendering unnecessary the laborious method of preparing glucosamine sulphate which is used as the starting product in the synthesis of glucosamine-SP.

In the method of the present invention, as defined by the appended claims, in place of glucosamine sulphate and sodium chloride, the starting products are glucosamine hydrochloride and the sulphate of the metal to be inserted in the composition of the mixed salt.

When reacted in the correct stoichiometric ratios and in reaction conditions similar to those described in the U.S. Pat. No. 4,642,340, these give rise directly to a product which corresponds exactly to glucosamine-SP, in the case of a combination of glucosamine hydrochloride and sodium sulphate, or to an analogue thereof in the case of a combination of glucosamine hydrochloride and the sulphate of another of the alkali-metals or alkaline-earths already mentioned. The technological progress associated with the method of the present invention is very clear in consideration of the advantages which it offers in comparison with the current state of the art.

These advantages may be summarised as follows:
1. Unlike glucosamine sulphate, glucosamine hydrochloride is a stable substance and does not therefore require particular precautions as far as its storage is concerned, in terms either of time or of temperature and humidity.
2. Costs are lower in terms of solvents and reagents (the synthesis starts directly from glucosamine hydrochloride without the need to synthesize glucosamine sulphate from glucosamine hydrochloride, in a vicious circle).
3. Energy costs are lower (again for the reasons given in point No. 2).
4. There is less wear of the equipment (again for the reasons given in point No. 2).
5. Less labour is used (the process takes place in a single step rather than in three steps).
6. A practically quantitative yield is obtained.

DESCRIPTION OF THE PREFERRED EMBODIMENTS

The preferred method of preparation according to the present invention comprises essentially the steps of dissolving the preselected sulphate, with stirring, in a quantity of distilled water variable between 4.5 and 6.5 (preferably 5) times the weight of the sulphate, at a temperature no higher than the boiling point of water, then reducing the temperature so that it does not exceed 60° C. (preferably 50° C.), adding the stoichiometric quantity of glucosamine hydrochloride, again with stirring, keeping the temperature constant until it is fully dissolved and, again with stirring and with the temperature being kept constant, precipitating the mixed glucosamine salt by the addition of a liquid precipitating agent which is miscible with water and in which the mixed glucosamine salt has a solubility no greater than 0.1% (w/v).

For example, acetone, ethanol, acetonitrile, tetrahydrofuran and dioxane may be used as precipitating agents added in volumes 5–7 (preferably 6) times greater than the volume of distilled water used to dissolve the starting salts. The precipitating agent is advantageously added over a period of 2.5 to 3.5 (preferably 3) hours, after which the resulting suspension of the mixed salt is kept, with slow stirring, for a further period ranging between 12 and 24 (preferably 18) hours at a temperature of between 25° and 35° C. (preferably 30° C.) to permit both complete precipitation and the correct crystal growth.

When the necessary period has elapsed, the reaction mass is cooled to a temperature of between 0° and 10° C. (preferably 5° C.) and the mixed salt thus obtained is filtered out and then dried in a forced-air oven at a temperature of between 45° and 65° C. (preferably 55° C.) for a period variable between 12 and 24 (preferably 18) hours.

EXAMPLE 1

Preparation of glucosamine-SP with the use of acetone as the precipitating agent 75 ml of distilled water were loaded into a four-necked flask with a usable capacity of 750 ml, with a paddle stirrer, thermometer and condenser and the temperature was brought to 70° C. by means of an electric heating bath. 14.21 g (0.1 moles - M.W. 142.06) of sodium sulphate previously dried to constant weight in an oven at 70° C. was added with moderate stirring (170 +/−10 revolutions per minute) and the mass was kept at 70° C. with stirring until dissolving was complete, which was achieved in about 20 minutes.

Upon completion of the dissolving, the temperature was reduced to 50° C. and 43.13 g (0.2 moles - M.W. 215.64) of glucosamine hydrochloride was added, the temperature being kept constant and stirring being maintained at 170 +/−10 revolutions per minute.

At this stage, a temperature greater than 60° C. could lead to yellowing of the reaction mass with a reduction both in the yield and in the purity of the final mixed salt.

In the conditions recommended, complete dissolving was achieved in about 45 minutes, after which the temperature was brought to 55° C. and precipitation was then carried out.

At temperatures below 50° C. too rapid a precipitation is brought about with the formation of crystalline agglomerations which may incorporate solvent and impurities, whereas above 60° C. undesirable yellowing of the suspension may occur. The precipitation was effected with the use of 450 cc of acetone which was dropped in over a period of 3 hours (with less than 2.5 hours the precipitation is too rapid and with more than 3.5 hours there are no practical advantages) and with stirring at 140 +/−10 revolutions per minute, which ensured the correct equilibrium between homogenisation of the phases and formation of the optimal quantity of crystallisation seeds.

Upon completion of the addition of the precipitating agent, the separation was complete and the precipitate was conditioned by reducing the temperature to 30° C. and by reducing the stirring speed to 100 +/−10 revolutions per minute, for a period of 18 hours.

In these conditions, a product of high purity was produced since the temperature of 30° C. favours the expulsion of any impurities and the reorganisation of crystals in the conditioning stage with absorption of any ions remaining in solution, whilst the gentle stirring enabled the entire precipitated mass to be kept constantly in contact with the solution without alteration of the uniformity of the crystalline mass.

The time indicated above is that required to allow the processes described above to be completed.

After 18 hours, the temperature was reduced to 5° C. by means of a water-ice bath and the crystalline mass obtained was filtered out with a Buchner filter.

After the moist filter cake had been well pressed in order to eliminate as much solvent as possible it was transferred into a forced-air oven and dried at 55° C. for 18 hours.

55.1 g (yield 96.1%) of creamy-white crystals with a bitter flavour were obtained.

The chemical and physical analytical characteristics of the glucosamine-SP obtained as described in Example 1 can be superimposed perfectly on those described in U.S. Pat. No. 4,642,340.

These characteristics are: Microanalysis for $C_{12}H_{28}Cl_2N_2Na_2SO_{14}$:

|  | % theoretical | % found |
| --- | --- | --- |
| Carbon | 25.14 | 25.23 |
| Hydrogen | 4.92 | 4.86 |
| Nitrogen | 4.88 | 4.97 |

Titre of glucosamine: 97.5–102.5% (potentiometric titre with NaOH in an aqueous medium).
Titre of sulphates: 97.5–102.5% (complexometric titre with EDTA in an $NH_3$ basic medium after precipitation with $BaCl_2$).
Titre of chlorides: 97.5–102.5% (argentometric titre).
Titre of sodium: 97.5–102.5% (in atomic absorption)
Appearance, colour, odour: Crystalline powder of pale cream colour, odourless and with a strongly bitter flavour.
Solubility (25° C. - w/v): Very soluble (about 40%): Water Slightly soluble (about 1%): Methanol Very slightly soluble (about 0.03%): Ethanol Practically insoluble (<0.01%): Acetone, acetonitrile, tetrahydrofuran, dioxane
Insoluble: Benzene chloroform, carbon tetrachloride, methylene chloride, ligroin, ethyl ether.
pH: The pH of a saturated aqueous solution of glucosamine-SP at 20° C. is 3 +/−0.2.
Partition coefficient: The partition coefficient of Glucosamine- SP determined at 25° C. in phosphate buffer (pH 6.8)/n-octanol has a practically infinite value.
Melting point: >300° C. (with partial decomposition above 200° C.).
Specific Rotation: 52 +/−0.2° (in equilibrium in 10% aqueous solution).

Roentgenographic investigation carried out both on samples of glucosamine-SP prepared according to the method described in the present patent application and on samples prepared according to the U.S. Pat. No. 4,642,340 showed that there was no difference between the two substances from a crystallographic point of view.

In fact, upon examination, the angular values and the intensity sequences of the diffraction patterns (Debye) of powders of the samples of the two types could be superimposed perfectly and were therefore indistinguishable.

EXAMPLE 2

Preparation of glucosamine-SP with the use of ethanol as the precipitating agent The method described in Example 1 was followed with the use of absolute ethanol instead of acetone. 54.3 g (94.7%) of glucosamine-SP having the same characteristics as described in Example 1 were obtained.

EXAMPLE 3

Preparation of glucosamine-SP with the use of acetonitrile as the precipitating agent The method described in Example 1 was followed, with the use if acetonitrile instead of acetone. 55.3 g (96.5%) of glucosamine-SP having the same characteristics as described in Example 1 were obtained.

EXAMPLE 4

Preparation of glucosamine-SP with the use of tetrahydrofuran as the precipitating agent The method described in Example 1 was followed, with the use of tetrahydrofuran instead of acetone. 53.7 g (93.7%) of glucosamine-SP having the same characteristics as described in Example 1 were obtained.

EXAMPLE 5

Preparation of glucosamine-SP with the use of dioxane as the precipitating agent The method described in Example 1 was followed, with the use of dioxane instead of acetone. 53.4 g (93.1%) of glucosamine-SP having the same characteristics as described in Example 1 were obtained.

EXAMPLE 6

Preparation of the mixed salt starting with glucosamine hydrochloride and potassium sulphate Exactly the same method as described in Example 1 was followed, the sodium sulphate being replaced by 17.43 g (0.1 moles - M.W. 174.3) of potassium sulphate.

58.9 g (yield 97.3%) of creamy-white crystals with a bitter flavour and having the following chemical and physical analytical characteristics were obtained: Microanalysis for $C_{12}H_{28}Cl_2N_2K_2SO_{14}$:

|          | % theoretical | % found |
|----------|---------------|---------|
| Carbon   | 23.80         | 23.94   |
| Hydrogen | 4.66          | 4.60    |
| Nitrogen | 4.63          | 4.67    |

Titre of glucosamine: 97.5–102.5% (potentiometric titre with NaOH in an aqueous medium).
Titre of sulphates: 97.5–102.5% (complexometric titre with EDTA in an $NH_3$ basic medium after precipitation with $BaCl_2$).
Titre of chlorides: 97.5–102.5% (argentometric titre).
Titre of potassium: 97.5–102.5% (in atomic absorption)
Appearance, colour, odour: Crystalline powder of pale cream colour, odourless and with a strongly bitter flavour.
Solubility (25° C. - w/v):
Very soluble (about 40%): water
Slightly soluble (about 1%): Methanol
Very slightly soluble (about 0.03%): Ethanol
Practically insoluble (<0.01%): Acetone, acetonitrile, tetrahydrofuran, dioxane
Insoluble: Benzene, chloroform, carbon tetrachloride, methylene chloride, ligroin, ethyl ether.
pH: The pH of a saturated aqueous solution of the mixed salt at 20° C. is 3 +/−0.2.
Partition coefficient: The partition coefficient of the mixed salt determined at 25° C. in phosphate buffer (pH 6.8)/n-octanol has a practically infinite value.
Melting point: >300° C. (with partial decomposition above 200° C.).
Specific Rotation: 49 +/−0.2° (in equilibrium in 10% aqueous solution).

EXAMPLE 7

Preparation of the mixed salt from glucosamine hydrochloride and calcium sulphate dihydrate.

Exactly the same method as described in Example 1 was followed, the sodium sulphate being replaced by 15.42 g of calcium sulphate dihydrate (0.1 moles - M.W. 154.16).

55.6 g (yield 98%) of creamy-white crystals having the following chemical and physical analytical characteristics were obtained: Microanalysis for $C_{12}H_{28}Cl_2N_2CaSO_{14}$:

|          | % theoretical | % found |
|----------|---------------|---------|
| Carbon   | 25.40         | 25.20   |
| Hydrogen | 4.97          | 5.07    |
| Nitrogen | 4.94          | 4.87    |

Titre of glucosamine: 97.5–102.5% (potentiometric titre with NaOH in an aqueous medium).
Titre of sulphates: 97.5–102.5% (complexometric titre with EDTA in an $NH_3$ basic medium after precipitation with $BaCl_2$) .
Titre of chlorides: 97.5–102.5% (argentometric titre).
Titre of calcium: 97.5–102.5% (in atomic absorption)
Appearance, colour, odour: Crystalline powder of pale cream colour, odourless and with a strongly bitter flavour.
Solubility (25° C. - w/v):
Very soluble (about 40%): water
Slightly soluble (about 1%): Methanol
Very slightly soluble (about 0.03%): Ethanol
Practically insoluble (<0.01%): Acetone, acetonitrile, tetrahydrofuran, dioxane
Insoluble: Benzene, chloroform, carbon tetrachloride, methylene chloride, ligroin, ethyl ether.
pH: The pH of a saturated aqueous solution of the mixed salt at 20° C. is 3 +/−0.2.
Partition coefficient: The partition coefficient of the mixed salt determined at 25° C. in phosphate buffer (pH 6.8)/n-octanol has a practically infinite value.
Melting point: >300° C. (with partial decomposition above 200° C.).
Specific Rotation: 52.5 +/−0.2° (in equilibrium in 10% aqueous solution).

EXAMPLE 8

Preparation of the mixed salt from glucosamine hydrochloride and magnesium sulphate heptahydrate.

Exactly the same method as described in Example 1 was followed, the sodium sulphate being replaced by 24.65 g (0.1 moles - M.W. 246.49) of magnesium sulphate heptahydrate.

52.2 g (94.6%) of creamy-white crystals of bitter flavour and having the following chemical and physical characteristics were obtained:
Microanalysis for $C_{12}H_{28}Cl_2N_2MgSO_{14}$:

|          | % theoretical | % found |
|----------|---------------|---------|
| Carbon   | 26.12         | 26.27   |
| Hydrogen | 5.11          | 5.01    |
| Nitrogen | 5.08          | 5.14    |

Titre of glucosamine: 97.5–102.5% (potentiometric titre with NaOH in an aqueous medium).
Titre of sulphates: 97.5–102.5% (complexometric titre with EDTA in an $NH_3$ basic medium after precipitation with $BaCl_2$).
Titre of chlorides: 97.5–102.5% (argentometric titre).
Titre of magnesium: 97.5–102.5% (in atomic absorption)
Appearance, colour, odour: Crystalline powder of pale cream colour, odourless and with a strongly bitter flavour.
Solubility (25° C. -w/v):
Very soluble (about 40%): water
Slightly soluble (about 1%): Methanol
Very slightly soluble (about 0.03%): Ethanol
Practically insoluble (<0.01%): Acetone, acetonitrile, tetrahydrofuran, dioxane
Insoluble: Benzene, chloroform, carbon tetrachloride, methylene chloride, ligroin, ethyl ether.
pH: The pH of a saturated aqueous solution of the mixed salt at 20° C. is 3 +/−0.2.
Partition coefficient: The partition coefficient of the mixed salt determined at 25° C. in phosphate buffer (pH 6.8)/n-octanol has a practically infinite value.
Melting point: >300° C. (with partial decomposition above 200° C.).
Specific Rotation: 54 +/−0.2° (in equilibrium in 10% aqueous solution).

From the stability point of view, the mixed salts of the present invention, like the glucosamine-SP described in the U.S. Pat. No. 4,642,340, were also found to be temperature- and moisture-resistant and thus easy to keep and perfectly usable in pharmaceutical techniques.

In fact, after 12 months at 25° C., and 60% relative humidity, preservation was perfect (see Tables 1 and 2) and further tests showed that only under extremely severe conditions, that is, 40° C. and 85% relative humidity was it possible, after 12 months, to observe a slight darkening of the colour and a slight reduction of the glucosamine titre (about 3–4%) which then remained constant under the same conditions of preservation for the next 12 months (see Tables 3 and 4).

TABLE 1

Comparison of the stability of Glucosamine-SP prepared according to the invention and prepared according to U.S. Pat. No. 4,642,340 at 25° C. and 60% R.H.

|  | Glucosamine-SP (invention) | | Glucosamine-SP U.S. Pat. No. 4,642,340 | |
|---|---|---|---|---|
| Time (months) | Appearance | Titre (%) | Appearance | Titre (%) |
| 0 | conforms (*) | 99.6 | conforms (*) | 100.2 |
| 3 | unchanged | 100.2 | unchanged | 100.4 |
| 6 | unchanged | 100.0 | unchanged | 99.7 |
| 9 | unchanged | 99.6 | unchanged | 99.9 |
| 12 | unchanged | 100.4 | unchanged | 100.3 |

TABLE 2

Stability of the other mixed glucosamine salts at 25° C. and 60% R.H.

Mixed salt of glucosamine hydrochloride with

| | Potassium sulphate | | Calcium suplhate | | Magnesium sulphate | |
|---|---|---|---|---|---|---|
| Time (months) | Appearance | Titre (%) | Appearance | Titre (%) | Appearance | Titre (%) |
| 0 | conforms (*) | 100.1 | conforms (*) | 99.6 | conforms (*) | 100.5 |
| 3 | unchanged | 100.3 | unchanged | 99.8 | unchanged | 100.1 |
| 6 | unchanged | 99.8 | unchanged | 100.1 | unchanged | 99.8 |
| 9 | unchanged | 99.6 | unchanged | 99.7 | unchanged | 100.3 |
| 12 | unchanged | 100.3 | unchanged | 100.0 | unchanged | 100.6 |

TABLE 3

Comparison of the stability of Glucosamine-SP prepared according to the invention and prepared according to U.S. Pat. No. 4,642,340 at 40° C. and 85% R.H.

|  | Glucosamine-SP (invention) | | Glucosamine-SP U.S. Pat. No. 4,642,340 | |
|---|---|---|---|---|
| Time (months) | Appearance | Titre (%) | Appearance | Titre (%) |
| 0 | conforms (*) | 99.6 | conforms (*) | 100.2 |
| 3 | unchanged | 99.8 | unchanged | 99.7 |
| 6 | unchanged | 100.3 | unchanged | 99.9 |
| 9 | unchanged | 100.2 | unchanged | 100.1 |
| 12 | sl.yellowing | 96.8 | sl.yellowing | 96.4 |
| 18 | unchanged | 97.1 | unchanged | 96.3 |
| 24 | unchanged | 96.6 | unchanged | 96.9 |

TABLE 4

Stability of the other mixed glucosamine salts at 40° C. and 85% R.H.

Mixed salt of glucosamine hydrochloride with

| | Potassium sulphate | | Calcium sulphate | | Magnesium sulphate | |
|---|---|---|---|---|---|---|
| Time (months) | Appearance | Titre (%) | Appearance | Titre (%) | Appearance | Titre (%) |
| 0 | conforms (*) | 100.1 | conforms (*) | 99.6 | conforms (*) | 100.5 |
| 3 | unchanged | 100.3 | unchanged | 99.4 | unchanged | 100.6 |
| 6 | unchanged | 99.8 | unchanged | 100.0 | unchanged | 100.1 |
| 9 | unchanged | 100.0 | unchanged | 99.6 | unchanged | 100.2 |
| 12 | sl. yellowing | 95.7 | sl. yellowing | 94.9 | sl. yellowing | 97.4 |
| 18 | unchanged | 96.2 | unchanged | 94.7 | unchanged | 97.7 |
| 24 | unchanged | 95.5 | unchanged | 94.8 | unchanged | 97.3 |

(*): Crystalline powder of pale cream colour.

What is claimed is:

1. A method of preparing a therapeutically active crystalline form of glucosamine sulphate which is stable at ambient temperature and humidity and corresponds to the empirical formula:

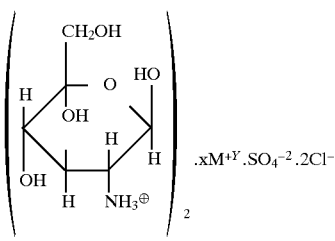

(I)

in which M represents a metal selected from the group consisting of Na, K, Ca, and Mg, x=1 if y=2, and x=2 if y=1, wherein glucosamine hydrochloride and a sulphate of a metal selected from the group consisting of Na, K, Ca, and Mg are used as the starting materials, the method comprising directly reacting said glucosamine hydrochloride and said sulphate in the stoichiometric ratio defined by formula (I), in an aqueous solvent, and precipitating said stable crystalline form of glucosamine sulphate by addition of a liquid precipitating agent miscible with water.

2. A method according to claim 1, comprising the steps of:
a) dissolving the sulphate defined above, with stirring, in a quantity of from 4.5 to 6.5 parts by weight of distilled water per part by weight of sulphate,
b) dissolving the stoichiometric quantity of glucosamine hydrochloride in the solution thus obtained, at a temperature no greater than 60° C., with stirring,
c) precipitating the stable crystalline form by the addition of a liquid precipitating agent which is miscible with water and in which the crystalline form has a solubility no greater than 0.1% (w/v), with stirring,
d) completing the precipitation by reducing the temperature of the mixture, and e) recovering the precipitated crystalline form.

3. A method according to claim 1 in which the liquid precipitating agent is selected from the group consisting of acetone, ethanol, acetonitrile, tetrahydrofuran and dioxane.

4. A method according to claim 1, in which the liquid precipitating agent is added in a proportion of from 5 to 7 parts by volume relative to the volume of aqueous solvent, over a period of from 2.5 to 3.5 hours.

5. A method according to claim 1, in which the stable crystalline form recovered is dried at a temperature of from 45° to 65° C.

* * * * *